(12) United States Patent
Okubo et al.

(10) Patent No.: US 8,225,199 B2
(45) Date of Patent: Jul. 17, 2012

(54) MEDICAL-INFORMATION DISPLAY APPARATUS AND MEDICAL-INFORMATION DISPLAY METHOD

(75) Inventors: Yosuke Okubo, Nasushiobara (JP); Hiroyuki Yamasaki, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 572 days.

(21) Appl. No.: 12/396,647

(22) Filed: Mar. 3, 2009

(65) Prior Publication Data
US 2009/0225102 A1    Sep. 10, 2009

(30) Foreign Application Priority Data
Mar. 4, 2008   (JP) ................................ 2008-053640

(51) Int. Cl.
*G06F 17/00* (2006.01)
*G09G 5/00* (2006.01)
(52) U.S. Cl. ........................................ 715/243; 345/619
(58) Field of Classification Search ......................... None
See application file for complete search history.

(56) References Cited

U.S. PATENT DOCUMENTS

| | | | | |
|---|---|---|---|---|
| 5,187,579 A * | 2/1993 | Hiyama | ........................ | 348/588 |
| 6,520,912 B1 * | 2/2003 | Brooks et al. | ................. | 600/437 |
| 7,885,440 B2 * | 2/2011 | Fram et al. | ..................... | 382/128 |
| 2005/0143641 A1 * | 6/2005 | Tashiro | ......................... | 600/407 |
| 2005/0238218 A1 * | 10/2005 | Nakamura | .................... | 382/128 |
| 2005/0259116 A1 * | 11/2005 | Araoka | ......................... | 345/619 |

FOREIGN PATENT DOCUMENTS

| | | | |
|---|---|---|---|
| EP | 2008578 A1 | * | 12/2008 |
| JP | 2006-6671 | | 1/2006 |

* cited by examiner

*Primary Examiner* — Joni Hsu
*Assistant Examiner* — David H Chu
(74) *Attorney, Agent, or Firm* — Oblon, Spivak, McClelland, Maier & Neustadt, L.L.P.

(57) ABSTRACT

In a medical-image observation apparatus, an image display-area display-control unit causes a display unit to display a main examination area for displaying a thumbnail of a medical image to be read, and an observation-image preparation area for displaying a thumbnail of a medical image selected as a medical image to be used for comparative image reading. After a reading-subject image display-control unit causes the display unit to display a thumbnail of a medical image to be read in the main examination area, upon receiving an operation of moving the medical image of which thumbnail is displayed in the main examination area into the observation-image preparation area, a comparison-subject image display-control unit specifies a medical image to be a comparison subject based on attribution information about the moved medical image, and causes the display unit to display a thumbnail of the specified medical image.

10 Claims, 15 Drawing Sheets

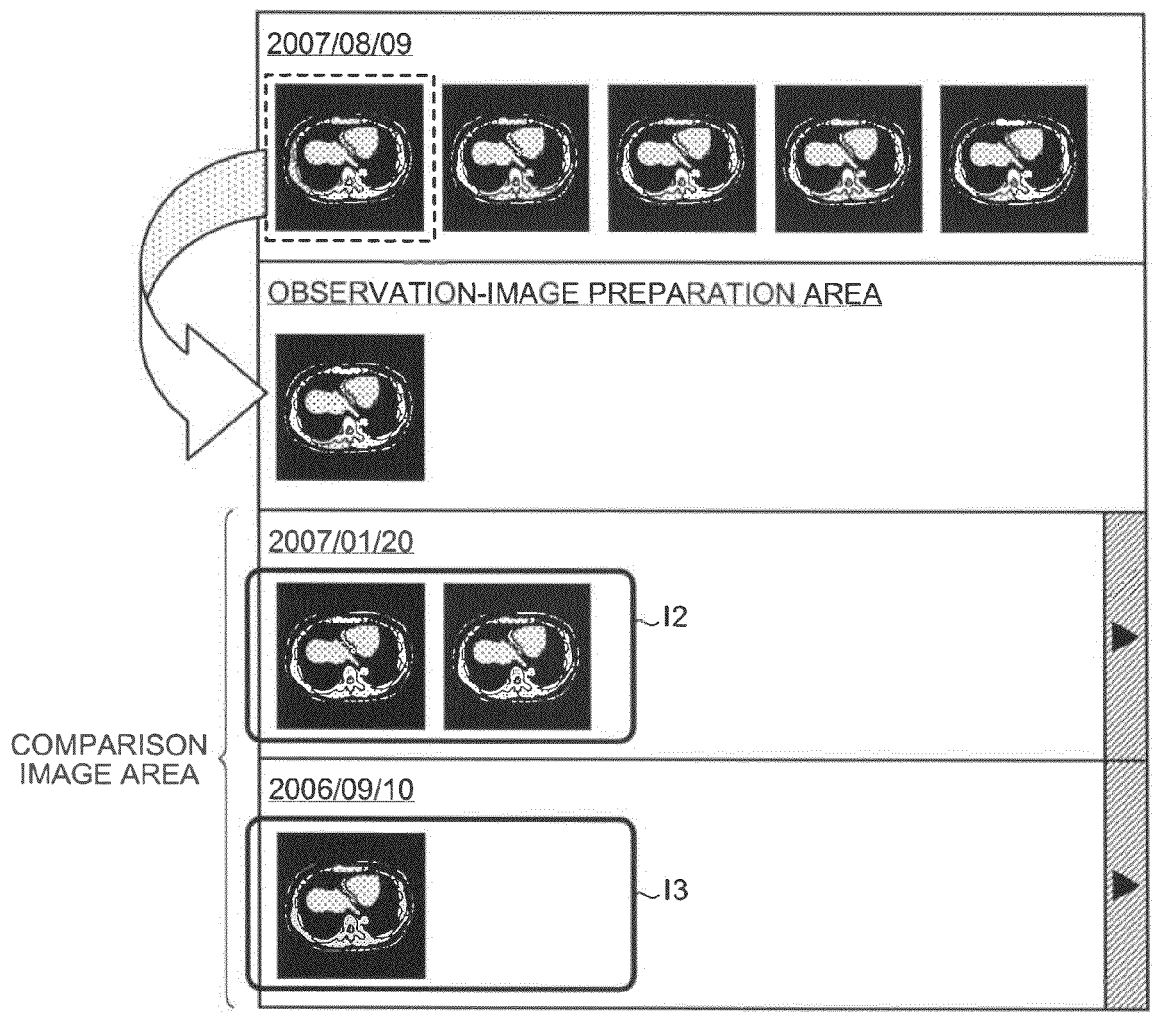

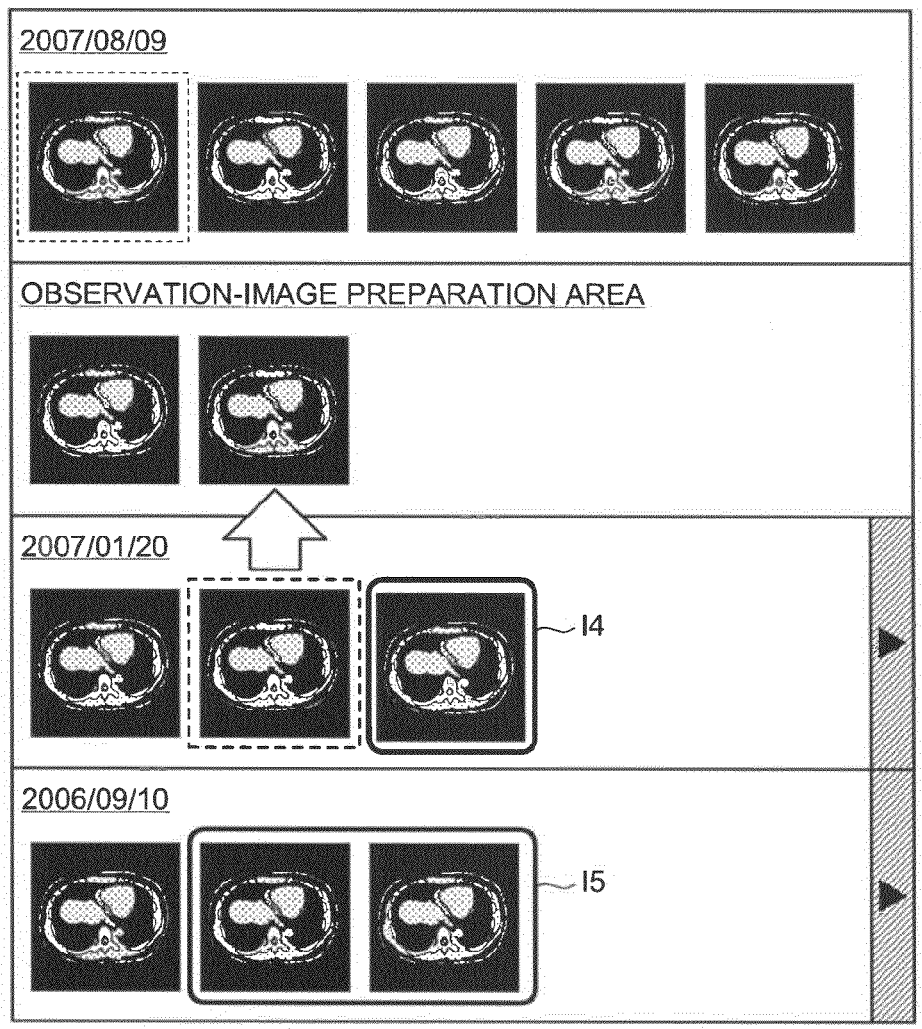

FIG.16A

| ATTRIBUTION INFORMATION | IMAGE LAYOUT | |
|---|---|---|
| X-RAY CT | <ATTRIBUTION INFORMATION> CURRENT CT IMAGE SERIES 1 | <ATTRIBUTION INFORMATION> PAST CT IMAGE SERIES 1 |
| | <ATTRIBUTION INFORMATION> CURRENT CT IMAGE SERIES 2 | <ATTRIBUTION INFORMATION> PAST CT IMAGE SERIES 2 |

FIG.16B

| ATTRIBUTION INFORMATION | IMAGE LAYOUT | | |
|---|---|---|---|
| X-RAY CT & ABDOMEN | <ATTRIBUTION INFORMATION> CURRENT CT IMAGE SERIES 1 | <ATTRIBUTION INFORMATION> PREVIOUS CT IMAGE ABDOMEN SERIES 1 | <ATTRIBUTION INFORMATION> SECOND PREVIOUS CT IMAGE ABDOMEN SERIES 1 |
| | <ATTRIBUTION INFORMATION> CURRENT CT IMAGE SERIES 2 | <ATTRIBUTION INFORMATION> PREVIOUS CT IMAGE ABDOMEN SERIES 2 | <ATTRIBUTION INFORMATION> SECOND PREVIOUS CT IMAGE ABDOMEN SERIES 2 |

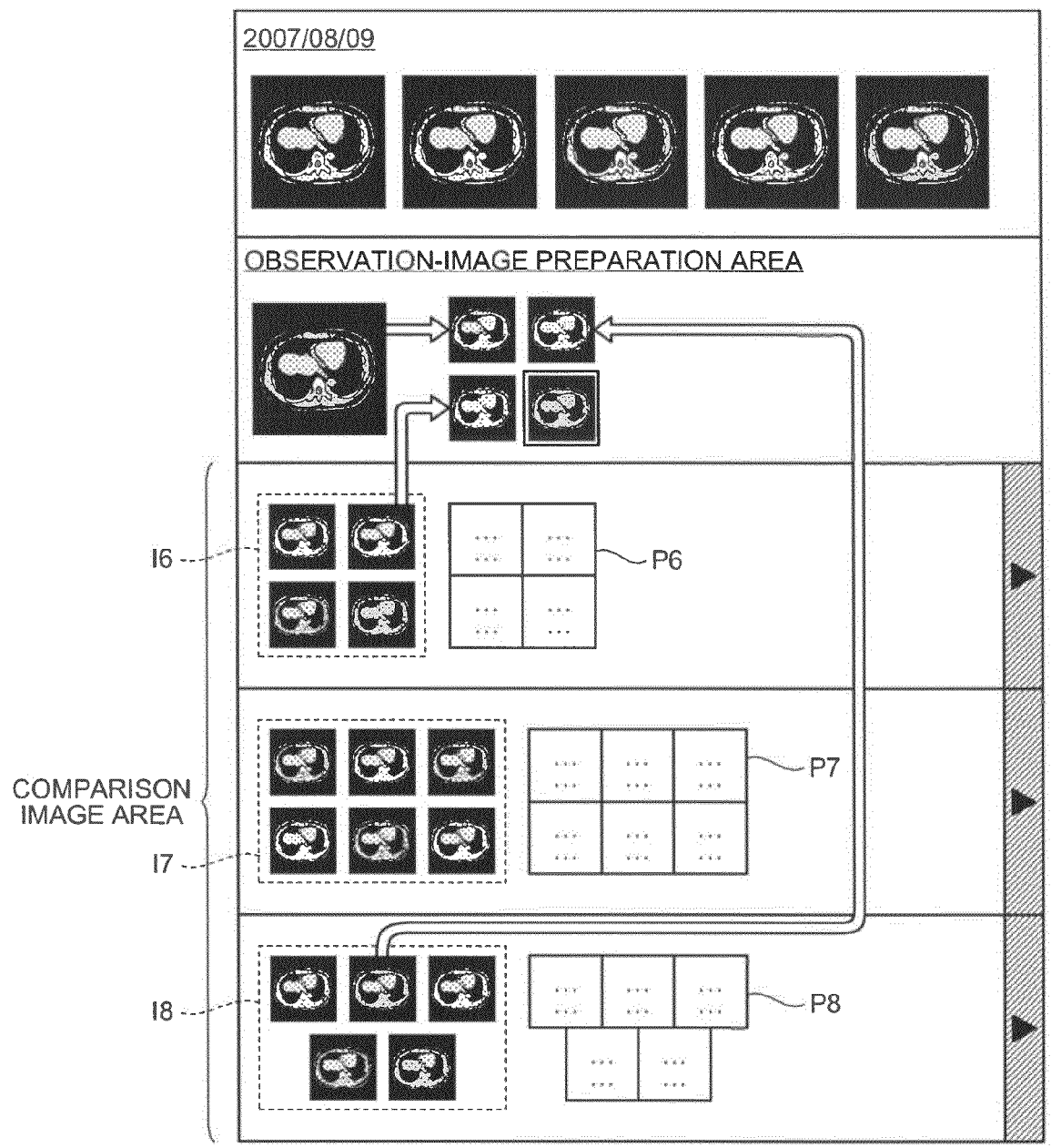

MEDICAL-INFORMATION DISPLAY APPARATUS AND MEDICAL-INFORMATION DISPLAY METHOD

CROSS-REFERENCE TO RELATED APPLICATIONS

This application is based upon and claims the benefit of priority from the prior Japanese Patent Application No. 2008-53640, filed on Mar. 4, 2008; the entire contents of which are incorporated herein by reference.

BACKGROUND OF THE INVENTION

1. Field of the Invention

The present invention relates to a medical-information display apparatus and a medical-information display method each configured to be used when reading a medical image, and particularly relates to display of medial images to be used for comparative image reading.

2. Description of the Related Art

According to conventional image reading of medical images, image reading is performed in many cases by comparing a medical image taken by a present examination with a medical image taken by the another examination. When performing such comparative image reading of medical images, an image reading person selects, from among medical images taken through other examinations, a medical image to be compared (hereinafter, a "comparison subject image") with a medical image to be read (hereinafter, a "reading subject image").

As a method of selecting a comparison subject image, for example, there is a method that a medical information apparatus displays thumbnails of a plurality of medical images that has been already taken by categorizing them with respect to attribution information, such as, examination date, modality (image diagnostic apparatus), and/or examination portion, and then an image reading person selects a comparison subject image from among the medical images of the displayed thumbnails (for example, see JP-A 2006-6671 (KOKAI)).

Usually, according to the method of displaying thumbnails of medical images, while thumbnails of medical images are displayed in a plurality of areas categorized with respect to attribution information, each of the areas is often reduced in size and displayed due to the display area that a medical information apparatus has. For this reason, in order to select a comparison subject image, an image reading person needs to repeat operations of developing each of the reduced areas, confirming whether the developed area includes a desired comparison subject image, and displaying the desired comparison subject image if included, or further developing and confirming another area if not included.

Consequently, according to the method, a number of steps need to be carried out until a comparison subject image is selected, and a user request to select a comparison subject image simply cannot be satisfied. Moreover, even if categorized areas are not reduced in size, the image reading person needs to expend much time and effort in order to find a comparison subject image from among all images included in the categorized areas.

SUMMARY OF THE INVENTION

According to one aspect of the present invention, a medical information-display apparatus includes a display unit that displays a main examination area for displaying a thumbnail of a medical image to be read, and an observation-image preparation area for displaying a thumbnail of a medical image selected as a medical image to be used for image reading; and a display control unit that controls a display of medical information onto the display unit, wherein the display control unit causes the display unit to display in the main examination area a thumbnail of a medical image to be read, when receiving an operation of displaying in the observation-image preparation area the medical image of which thumbnail is displayed in the main examination area, the display control unit specifies a medical image to be a comparison subject based on attribution information about the medical image of displayed thumbnail, and causes the display unit to display a thumbnail of specified medical image.

According to another aspect of the present invention, a medical information-display method includes displaying on a display unit a main examination area for displaying a thumbnail of a medical image to be read and an observation-image preparation area for displaying a thumbnail of a medical image selected as a medical image to be used for image reading; displaying a thumbnail of a medical image to be read on the main examination area; and specifying a medical image to be a comparison subject based on attribution information about the medical image, and causing the display unit to display a thumbnail of the specified medical image, when receiving an operation of displaying in the observation-image preparation area the medical image of which thumbnail is displayed in the main examination area.

BRIEF DESCRIPTION OF THE DRAWINGS

FIG. 5 is a schematic diagram (1) for explaining display of comparison subject images controlled by a comparison-subject image display-control unit shown in FIG. 2;

FIG. 6 is a schematic diagram that depicts an example of setting information for determining a search key based on attribution information according to the first embodiment;

FIG. 7 is a schematic diagram (2) for explaining display of comparison subject images controlled by the comparison-subject image display-control unit;

FIG. 8 is a schematic diagram that depicts an example of setting information for determining a search key based on a combination of attribution information according to the first embodiment;

FIGS. 16A and 16B are schematic diagrams for explaining information to be stored by a display-mode condition storage unit according to the second embodiment; and FIGS. 17 to 20 are schematic diagrams for explaining display of comparison subject images controlled by a comparison-subject image display-control unit according to the second embodiment.

DETAILED DESCRIPTION OF THE INVENTION

Exemplary embodiments of a medical-information display apparatus and a medical information display method according to the present invention will be explained below in detail with reference to the accompanying drawings. Explained in the following embodiments is a case where the present invention is applied to a medical-image observation apparatus connected to a medical image diagnostic system.

Figure 1:
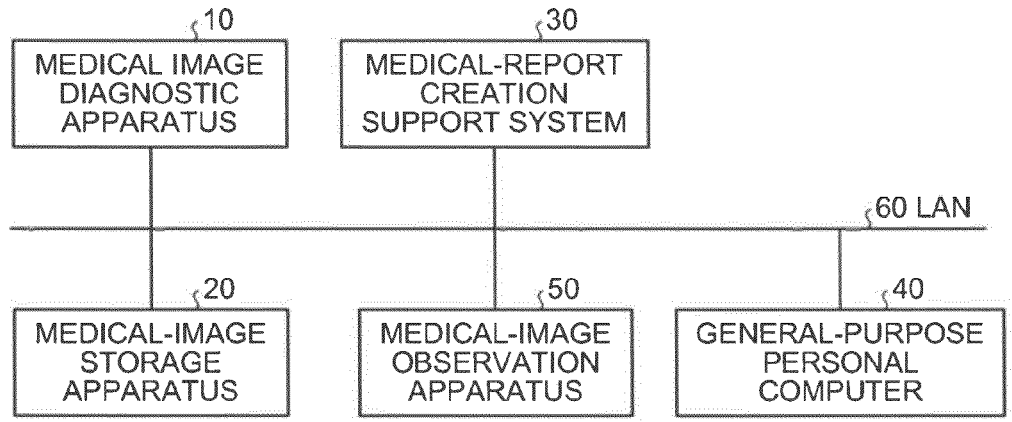
FIG. 1 is a system configuration diagram that depicts a configuration of a medical diagnostic-imaging system according to a first embodiment of the present invention.

First of all, a configuration of a medical image diagnostic system according to a first embodiment of the present invention is explained below. FIG. 1 is a system configuration diagram that depicts a configuration of the medical image diagnostic system according to the first embodiment. As shown in FIG. 1, the medical image diagnostic system includes a medical image diagnostic apparatus 10, a medical-image storage apparatus 20, a medical-report creation support system 30, a general-purpose personal computer 40, and a medical-image observation apparatus 50, which are connected one another via a Local Area Network (LAN) 60.

The medical image diagnostic apparatus 10 is an apparatus that takes a medical image, such as a Magnetic Resonance Imaging (MRI) apparatus, or an X-ray Computed Tomography (CT) apparatus. The medical-image storage apparatus 20 stores therein a medical image taken by the medical image diagnostic apparatus 10.

The medical-report creation support system 30 supports creation of a medical report performed by an image-reading doctor, and manages the created medical report as report information. The general-purpose personal computer 40 is a computer for general purposes in which various software programs, such as a Web browser, are installed.

The medical-image observation apparatus 50 acquires and displays a medical image stored by the medical-image storage apparatus 20 and report information managed by the medical-report creation support system 30. The medical-image observation apparatus 50 is configured to be used when an image-reading doctor performs comparative image reading of medical images.

According to the first embodiment, the medical-image observation apparatus 50 is configured to display on a display unit a main examination area for displaying a thumbnail of a medical image to be read, and an observation-image preparation area for displaying a thumbnail of a medical image selected as a medical image to be used for comparative image reading. After a thumbnail of a medical image to be read is displayed in the main examination area, when receiving an operation of displaying the medical image in the observation-image preparation area, the medical-image observation apparatus 50 specifies a medical image to be a comparison subject based on attribution information about the medical image of the displayed thumbnail, and causes the display unit to display a thumbnail of the specified medical image. According to the medical-image observation apparatus 50 of the first embodiment, an image reading person can easily select a medical image to be a comparison subject when performing comparative image reading of medical images without carrying out a procedure of finding a comparison subject image by developing a thumbnail display area.

The medical-image observation apparatus 50 is specifically explained below. Explained below is a case where an operator performs an operation of moving a medical image into the observation-image preparation area (for example, drag-and-drop by using a mouse), as an example of "an operation of displaying a medical image in the observation-image preparation area".

Figure 2:
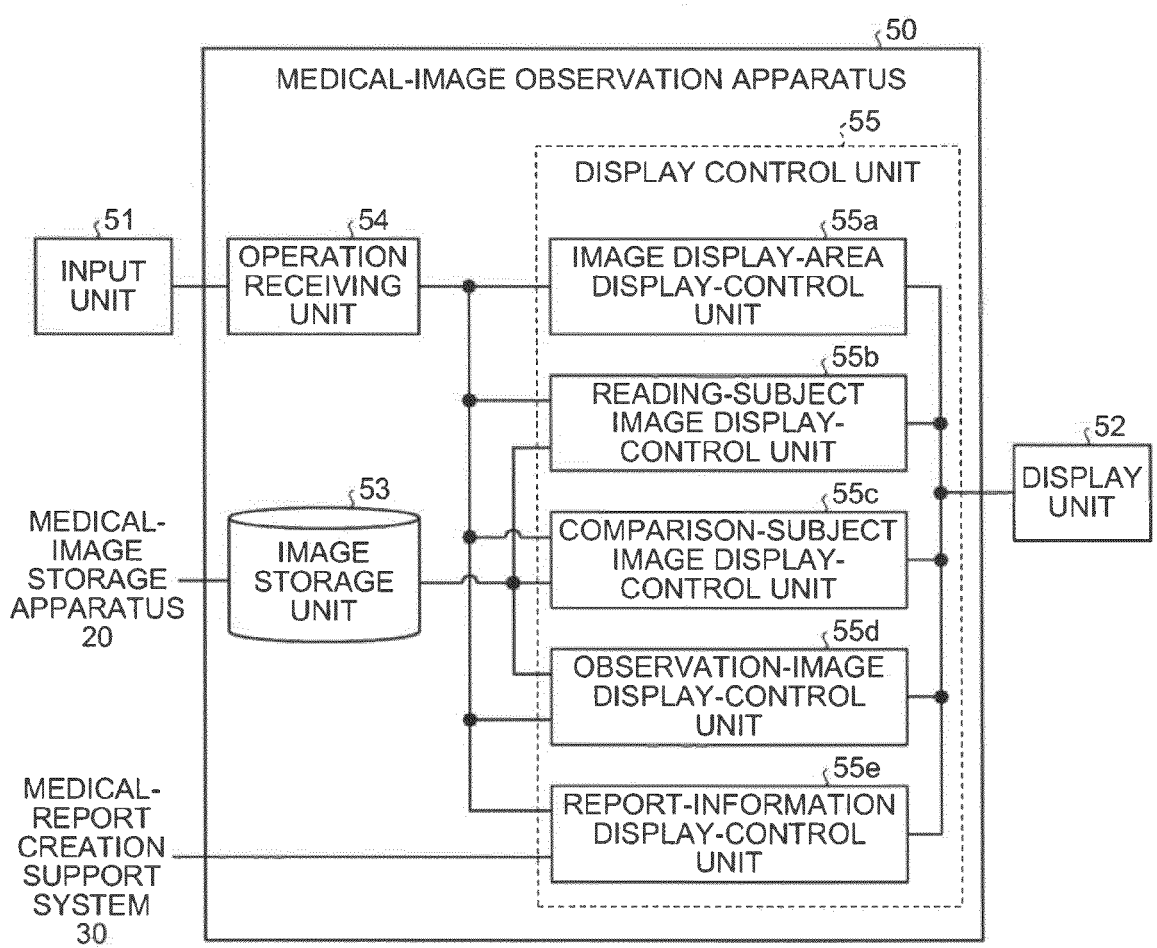
FIG. 2 is a functional block diagram that depicts a configuration of a medical-image observation apparatus according to the first embodiment.

FIG. 2 is a functional block diagram that depicts a configuration of the medical-image observation apparatus 50 according to the first embodiment. As shown in FIG. 2, the medical-image observation apparatus 50 includes an input unit 51, a display unit 52, an image storage unit 53, an operation receiving unit 54, and a display control unit 55.

The input unit 51 receives input of various information, and includes, for example, a pointing device, such as a mouse or a trackball, and a keyboard. The display unit 52 displays various information, and includes, for example, a Cathode Ray Tube (CRT) display or a liquid crystal display.

The image storage unit 53 stores therein a medical image taken by the medical image diagnostic apparatus 10. According to the first embodiment, it is assumed that medical images about a patient who is to be a reading subject have already been acquired and stored in the image storage unit 53. Needless to say, the medical images can be searched out and acquired from the medical-image storage apparatus 20 as necessary. The operation receiving unit 54 receives various operations and various requests from the operator via the input unit 51.

The display control unit 55 controls display of medical information onto the display unit 52. The display control unit 55 includes an image display-area display-control unit 55a, a reading-subject image display-control unit 55b, a comparison-subject image display-control unit 55c, an observation-image display-control unit 55d, and a report-information display-control unit 55e.

Figure 3:
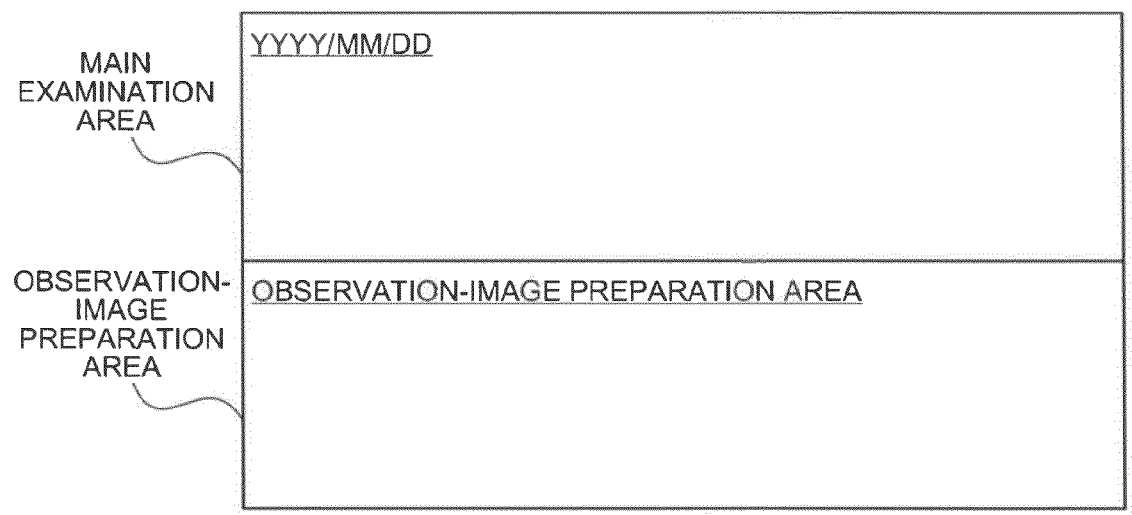
FIG. 3 is a schematic diagram for explaining display of image display areas controlled by an image display-area display-control unit shown in FIG. 2.

The image display-area display-control unit 55a causes the display unit 52 to display an image display area for displaying a thumbnail of a medical image. FIG. 3 is a schematic diagram for explaining display of image display areas controlled by the image display-area display-control unit 55a. As shown in FIG. 3, specifically, when receiving an operation of selecting an image-reading subject examination via the operation receiving unit 54, the image display-area display-control unit 55a causes the display unit 52 to display the main examination area for displaying a thumbnail of a reading subject image, and the observation-image preparation area for selecting a medical image to be used for comparative image reading.

Figure 4:
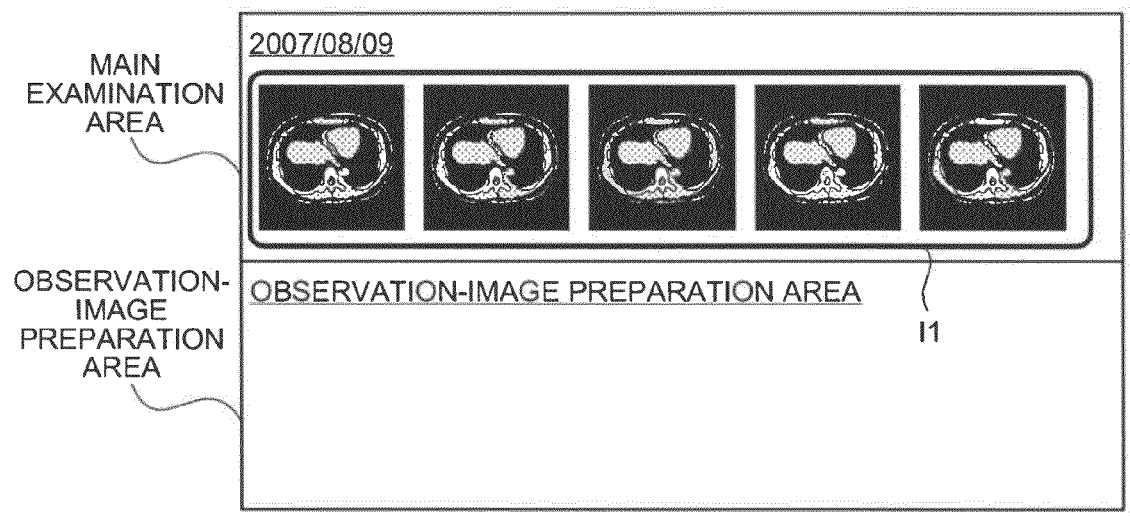
FIG. 4 is a schematic diagram for explaining display of reading subject images controlled by a reading-subject image display-control unit shown in FIG. 2.

Returning to FIG. 2, the reading-subject image display-control unit 55b causes the display unit 52 to display a reading subject image in response to an operation by the operator. FIG. 4 is a schematic diagram for explaining display of reading subject images controlled by the reading-subject image display-control unit 55b.

Specifically, as shown in FIG. 4, when receiving an operation of selecting an examination of an image reading subject via the operation receiving unit 54, the reading-subject image display-control unit 55b searches for medical images included in a series of the selected examination from among medical images stored by the image storage unit 53, and conducts thumbnail display of the found medical images as reading subject images in the main examination area displayed with control by the image display-area display-control unit 55a (see I1 shown in FIG. 4).

When displaying the reading subject images in thumbnail, the reading-subject image display-control unit 55b searches out all medical images related to a patient of the examination selected by the operator (including medical images taken through examinations other than the selected examination) from among medical images stored by the image storage unit 53, and creates thumbnails of the found medical images. The reading-subject image display-control unit 55b then stores the created thumbnails in an internal memory as comparison subject images.

The reading-subject image display-control unit 55b does not need to create thumbnail images of all of the medical images, and can be configured to store only supplementary information (attribution information) in the internal memory, and to store only thumbnail images of required medical images in the internal memory. Alternatively, the reading-subject image display-control unit 55b can be configured to search for only required medical images, and to create thumbnail images of the found medical images.

Returning to FIG. 2, the comparison-subject image display-control unit 55c causes the display unit 52 to display a comparison subject image in response to an operation by the operator. FIG. 5 is a schematic diagram (1) for explaining display of comparison subject images controlled by the comparison-subject image display-control unit 55c.

Specifically, as shown in FIG. 5, when receiving an operation of moving a reading subject image of which thumbnail is displayed in the main examination area into the observation-image preparation area via the operation receiving unit 54, the comparison-subject image display-control unit 55c specifies comparison subject images stored in the internal memory based on attribution information about the reading subject image, and causes the display unit 52 to display the specified comparison subject images from examination to examination. When displaying the comparison subject images, as shown in FIG. 5, the comparison-subject image display-control unit 55c conducts display of a plurality of comparison image areas partitioned from examination to examination, and then causes the display unit 52 to display respective comparison subject images in the comparison image areas (see I2 and I3 shown in FIG. 5).

When the reading subject image is moved into the observation-image preparation area, if the operator performs a particular operation, for example, a right drag with the mouse, the comparison-subject image display-control unit 55c can be configured not to perform narrowing down based on attribution information about the medical image that is moved.

The display of comparison subject images is explained below in detail. Upon receiving an operation of moving a reading subject image into the observation-image preparation area, the comparison-subject image display-control unit 55c first determines information to be a search key for searching for comparison subject images based on attribution information about the moved reading subject image. When performing the determination, as information to be a search key, information unique to each medical image, for example, modality, a scan portion, or a scanning condition, or information about a report using a medical image as a key image is to be used.

Specifically, the comparison-subject image display-control unit 55c determines information to be a search key based on setting information stored in advance in a storage unit that is not shown in FIG. 2. FIG. 6 is a schematic diagram that depicts an example of setting information for determining a search key based on attribution information. As shown in FIG. 6, information on a search key for searching for a comparison subject associated with attribution information about a medical image moved into the observation-image preparation area is set in the setting information with respect to each of a plurality of attribution information.

For example, it is assumed that setting information shown in FIG. 6 is stored. When the modality of a moved reading subject image is "X-ray CT apparatus", the comparison-subject image display-control unit 55c sets information to be a search key to "scan portion or modality". Or, for example, when a scan portion of a moved reading subject image is "head", the comparison-subject image display-control unit 55c sets information to be a search key to "modality or scanning condition".

Subsequently, the comparison-subject image display-control unit 55c acquires a concrete value of the information as the search key by referring to supplementary information on the reading subject image moved into the observation-image preparation area. The comparison-subject image display-control unit 55c then searches for comparison subject images that have the acquired concrete value as supplementary information from among comparison subject images stored in the internal memory, and conducts display of the found comparison subject images in a comparison image area.

For example, it is assumed that stored as setting information is a definition that a search key is "scan portion or modality" when the modality of a moved reading subject image is "X-ray CT apparatus". In such case, for example, when a reading subject image of the head taken by an X-ray CT apparatus is moved into the observation-image preparation area, the comparison-subject image display-control unit 55c acquires a concrete value indicating that a scan portion is "head", and a concrete value indicating that the modality is "X-ray CT apparatus", by referring to supplementary information on the moved reading subject image.

The comparison-subject image display-control unit 55c then searches out medical images of the head and medical images taken by the X-ray CT apparatus from among the comparison subject images stored in the internal memory, and causes the display unit 52 to display the found images in the comparison image areas. In this way, as the comparison-subject image display-control unit 55c searches comparison subject images stored in the internal memory by using certain information as a search key, the number of comparison subject images to be displayed in the comparison image areas is narrowed down based on attribution information about the moved medical image.

Moreover, while at least one medical image is being displayed in the observation-image preparation area, when receiving an operation of moving another medical image into the observation-image preparation area, the comparison-subject image display-control unit 55c specifies a comparison subject image stored in the internal memory based on a combination of attribution information about the moved medical image and attribution information about the priorly displayed medical image, and causes the display unit 52 to display the specified comparison subject image in the comparison image area, from examination to examination.

FIG. 7 is a schematic diagram (2) for explaining display of comparison subject images controlled by the comparison-subject image display-control unit 55c. For example, as shown in FIG. 7, while reading subject images are being displayed in the observation-image preparation area, upon receiving an operation of moving a comparison subject image from a comparison image area into the observation-image preparation area via the operation receiving unit 54, the comparison-subject image display-control unit 55c specifies a comparison subject image stored in the internal memory based on a combination of attribution information about the moved comparison subject image and attribution information about the reading subject images that are priorly displayed, and causes the display unit 52 to display the specified comparison subject image in the comparison image area, from examination to examination (see I4 and I5 shown in FIG. 7).

The display of comparison subject images is explained below in detail. Upon receiving an operation of moving a medical image into the observation-image preparation area, the comparison-subject image display-control unit 55c first determines information to be a search key when searching for comparison subject images based on a combination of attribution information about the moved medical image and attribution information about the medical images that are priorly displayed. When performing the determination, information unique to each medical image, for example, modality, a scan portion, or a scanning condition, or information about a report using a medical image as a key image is used as information to be a search key, as described above.

Specifically, the comparison-subject image display-control unit 55c determines information to be a search key based on setting information stored in advance in a storage unit that is not shown in FIG. 2. FIG. 8 is a schematic diagram that depicts an example of setting information for determining a search key based on a combination of attribution information. As shown in FIG. 8, information in which a combination of attribution information about a medical image moved into the observation-image preparation area is associated with a search key for searching for a comparison subject is set in the setting information. Such setting information is manually or automatically stored based on, for example, a combination of medical images that were used for comparison in comparative image reading in the past.

For example, when setting information shown in FIG. 8 is stored, if the modality of the moved reading subject image is "X-ray CT apparatus" and the modality of the priorly displayed medical information is "Computed Radiography (CR) device", the comparison-subject image display-control unit 55c sets information to be a search key to "scan portion". Or, for example, if a scan portion of the moved medical image is "head", and a scan portion of the priorly displayed medical image is "abdomen", the comparison-subject image display-control unit 55c sets information to be a search key to "modality".

Subsequently, the comparison-subject image display-control unit 55c acquires a concrete value of the information as the search key by referring to each of supplementary information on the reading subject image moved into the observation-image preparation area and the priorly displayed medical image. The comparison-subject image display-control unit 55c then searches out a comparison subject image that has the acquired concrete value as supplementary information from among the comparison subject images stored in the internal memory, and causes the display unit 52 to display the found comparison subject image in the comparison image area.

For example, it is assumed that a definition such that "scan portion" is used as a search key when "X-ray CT apparatus" and "CR apparatus" are combined is stored as setting information. In such case, for example, when a medical image of the abdomen taken by a CR apparatus is moved into the observation-image preparation area while a medical image of the head taken by an X-ray CT apparatus is being displayed in the observation-image preparation area, the comparison-subject image display-control unit 55c acquires a concrete value indicating that a scan portion is "head", and a concrete value indicating that a scan portion is "abdomen", by referring to supplementary information on the respective medical images.

The comparison-subject image display-control unit 55c then searches out a medical image of the head and a medical image of the abdomen from among the comparison subject images stored in the internal memory, and causes the display unit 52 to display the respective found medical images in the comparison image areas. In this way, as the comparison-subject image display-control unit 55c searches the comparison subject images stored in the internal memory by using certain information as a search key, the number of comparison subject images to be displayed in the comparison image area is narrowed down based on a combination of attribution information about the moved medical image and attribution information about the priorly displayed medical image.

Explained above is a case where the comparison-subject image display-control unit 55c conducts display of the comparison image areas from examination to examination, and display of only the narrowed-down comparison subject images from examination to examination. In addition to this, for example, the comparison-subject image display-control unit 55c can be configured to conduct display of a user interface for each examination for displaying comparison subject images excluded from the narrowing-down as well as display of the comparison image areas and the narrowed-down comparison subject images.

Figure 9:
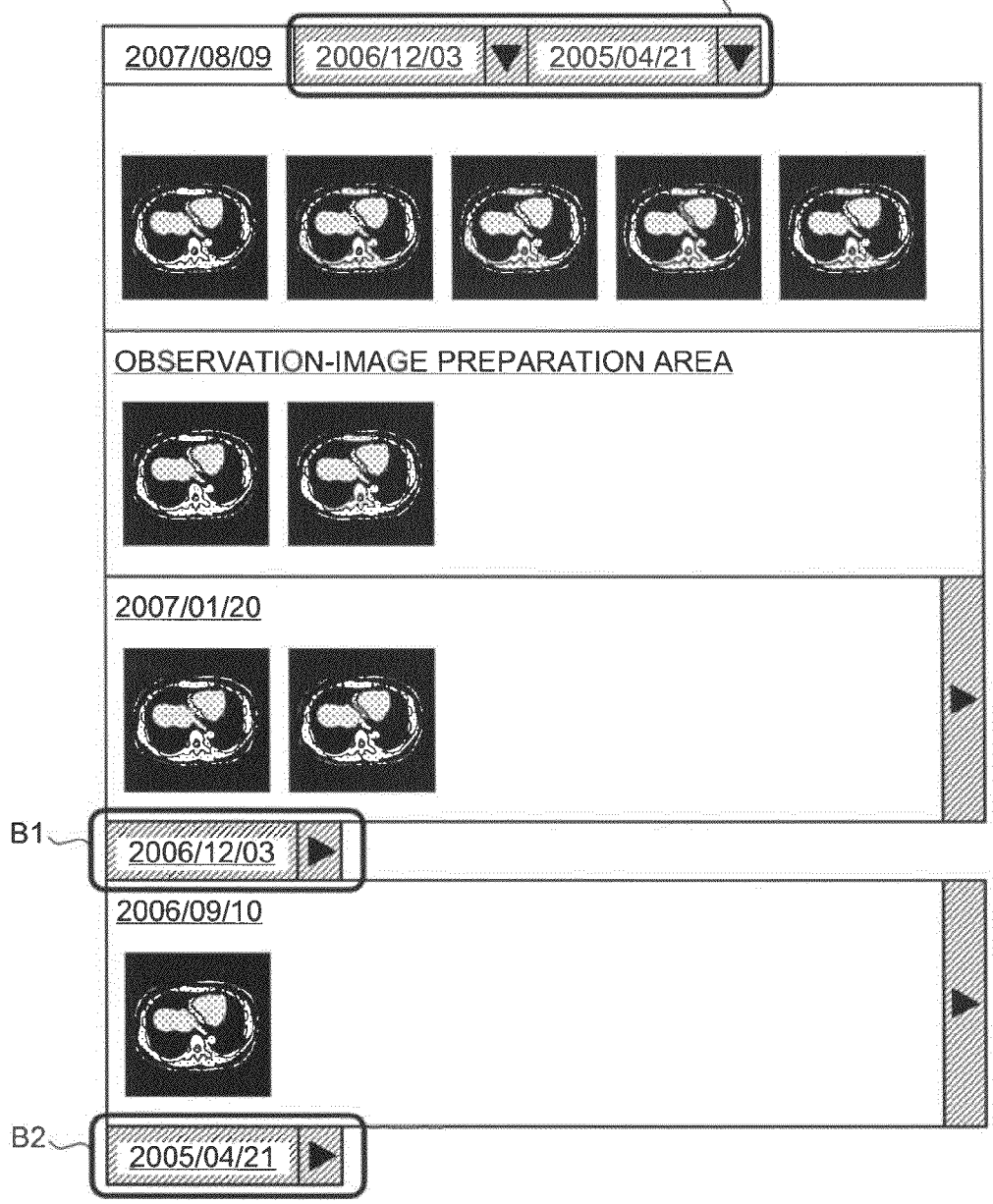
FIG. 9 is a schematic diagram (3) for explaining display of comparison subject images controlled by the comparison-subject image display-control unit.

FIG. 9 is a schematic diagram (3) for explaining display of comparison subject images controlled by the comparison-subject image display-control unit 55c. For example, as shown in FIG. 9, the comparison-subject image display-control unit 55c conducts display of buttons (see B1 and B2 shown in FIG. 9) and a tub (see T shown in FIG. 9) as a user interface.

Upon receiving an operation on a displayed user interface from the operator, the comparison-subject image display-control unit 55c conducts developed display of a comparison image area of an examination corresponding to the user interface, searches for a comparison subject image of the examination from among the medical images stored in the internal memory, and then causes the display unit 52 to display the found image in the developed comparison image area.

Figure 10:
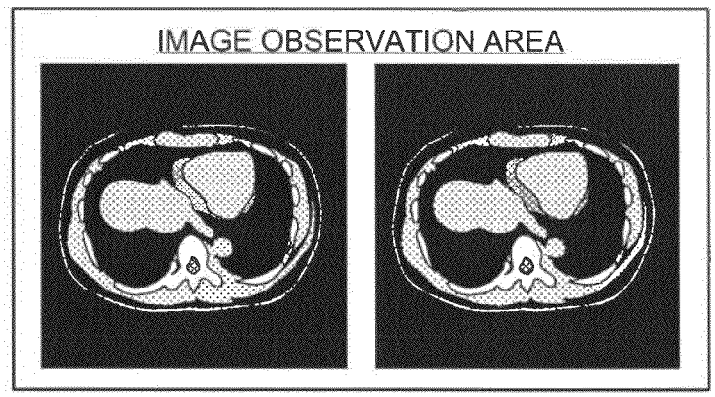
FIG. 10 is a schematic diagram for explaining enlarged display of a medical image controlled by an observation-image display-control unit shown in FIG. 2.

Returning to FIG. 2, the observation-image display-control unit 55d conducts enlarged display of a medical image of which thumbnail is displayed in the observation-image preparation area, in response to a request from the operator. FIG. 10 is a schematic diagram for explaining enlarged display of a medical image controlled by the observation-image display-control unit 55d.

Specifically, as shown in FIG. 10, upon receiving via the operation receiving unit 54 a display request to display an image observation area in which medical images for comparative image reading are to be displayed, the observation-image display-control unit 55d causes the display unit 52 to display the image observation area. The observation-image display-control unit 55d then acquires medical images of which thumbnails are displayed in the observation-image preparation area from the image storage unit 53, and causes the display unit 52 to display the acquired medical images in an enlarged scale in the displayed image observation area.

When displaying the medical images, the observation-image display-control unit 55d conducts enlarged display of the medical images by maintaining an image layout when the medical images are displayed in the observation-image preparation area. Although FIG. 10 depicts a case where the medical images are displayed in an enlarged scale in an image layout in which the medical images are arranged side by side, the image layout controlled by the observation-image display-control unit 55d is not limited to this. For example, the image layout can be configured such that images are vertically arranged, or such that a plurality images is displayed from left to right and top to bottom.

The report-information display-control unit 55e acquires information about a report associated with the medical image as a key image, and causes the display unit 52 to display the acquired information, upon receiving an operation of displaying a medical image in the observation image preparation area. Specifically, upon receiving an operation of moving a medical image into the observation-image preparation area via the operation receiving unit 54, the report-information display-control unit 55e acquires information about a report associated with the moved medical image as a key image from the medical-report creation support system 30. The report-information display-control unit 55e then conducts display of a thumbnail or an icon of the report based on the acquired information. The report-information display-control unit 55e can conduct display of the report itself instead of a thumbnail or an icon.

After that, upon receiving an operation of selecting the displayed thumbnail or the displayed icon, the report-information display-control unit 55e instructs the medical-report creation support system 30 to display a report corresponding to the selected thumbnail or the selected icon.

Figure 11:
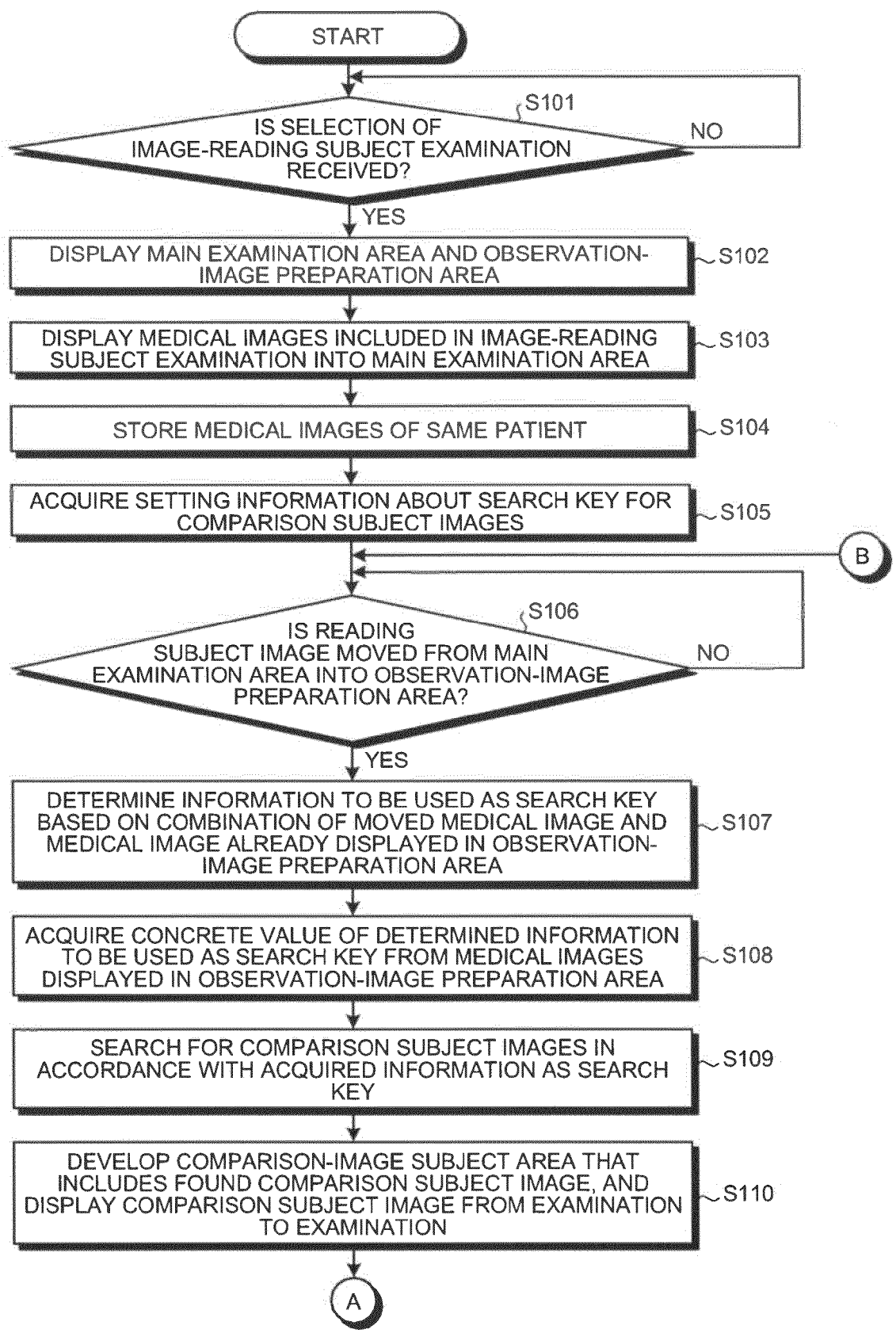
FIGS. 11 and 12 are flowcharts that depict a process procedure performed by the medical-image observation apparatus according to the first embodiment.
Figure 12:
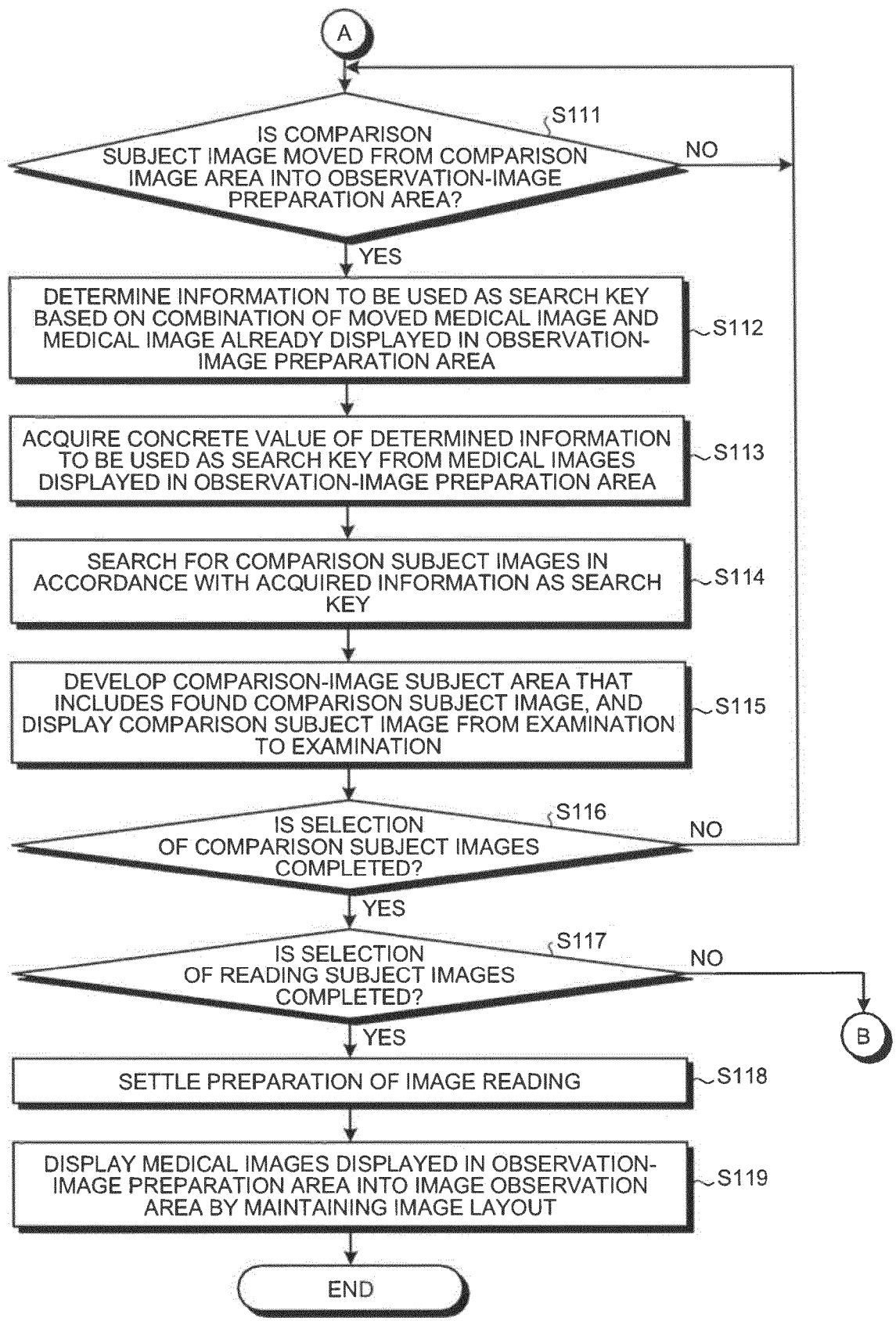

A process procedure performed by the medical-image observation apparatus 50 according to the first embodiment is explained below. FIGS. 11 and 12 are flowcharts (1) and (2) that depict a process procedure performed by the medical-image observation apparatus 50 according to the first embodiment. As shown in FIG. 11, according to the medical-image observation apparatus 50, when the image display-area display-control unit 55a receives a selection of an image-reading subject examination via the operation receiving unit 54 (Yes at Step S101), the image display-area display-control unit 55a conducts display of the main examination area and the observation-image preparation area (Step S102).

Subsequently, the reading-subject image display-control unit 55b searches for medical images included in the selected image-reading subject examination, causes the display unit 52 to display the found medical images as reading subject images in the main examination area (Step S103), further searches for medical images of the same patient, and stores the found medical images in the internal memory (Step S104). The comparison-subject image display-control unit 55c acquires setting information about a search key for comparison subject images (Step S105).

The reading-subject image display-control unit 55b does not need to store medical images of the same patient. For example, the reading-subject image display-control unit 55b can be configured to acquire only setting information and examination information necessary for searching for the medical images, and the comparison-subject image display-control unit 55c can be configured to acquire medical images based on the information acquired by the reading-subject image display-control unit 55b, when it is necessary to display the medical images. Accordingly, load caused by acquiring extra information can be reduced.

After that, When the comparison-subject image display-control unit 55c receives via the operation receiving unit 54 an operation of moving a reading subject image from the main examination area into the observation-image preparation area (Yes at Step S106), the comparison-subject image display-control unit 55c determines information to be used as a search key based on a combination of the moved medical image and a medical image that is already displayed in the observation-image preparation area (Step S107).

Subsequently, the comparison-subject image display-control unit 55c acquires a concrete value of the determined information to be used as a search key from the medical images displayed in the observation-image preparation area (Step S108), and searches for comparison subject images in accordance with the acquired concrete value as a search key (Step S109). The comparison-subject image display-control unit 55c then develops a comparison-image subject area that includes the found comparison subject image, and causes the display unit 52 to display the comparison subject image in the developed comparison image area, from examination to examination (Step S110).

After that, as shown in FIG. 12, when the comparison-subject image display-control unit 55c receives an operation of moving a comparison subject image from a comparison image area into the observation-image preparation area via the operation receiving unit 54 (Yes at Step S111), the comparison-subject image display-control unit 55c determines information to be used as a search key based on a combination of the moved medical image and the medical image that is already displayed in the observation-image preparation area (Step S112).

Subsequently, the comparison-subject image display-control unit 55c acquires a concrete value of the determined information to be used as a search key from the medical image displayed in the observation-image preparation area (Step S113), and searches for a comparison subject image in accordance with the acquired concrete value as a search key (Step S114). The comparison-subject image display-control unit 55c then develops a comparison-image subject area that includes the found comparison subject image, and causes the display unit 52 to display the comparison subject image in the developed comparison image area, from examination to examination (Step S115).

While the operator is performing the operation of moving a comparison subject image from a comparison image area into the observation-image preparation area (the operation at Step S111), the comparison-subject image display-control unit 55c repeats the processing at Steps S111 to S115 (No at Step S116); and when the selection of comparison subject images corresponding to a reading subject image is completed (Yes at Step S116), the comparison-subject image display-control unit 55c receives an operation of moving the next reading subject image (returns to Step S106).

While the operator is then performing the operation of moving a reading subject image from the main examination area into the observation-image preparation area (the operation at Step S106), the comparison-subject image display-control unit 55c repeats the processing at Steps S106 to S116 (No at Step S117); and when the selection of reading subject images is completed (Yes at Step S117), the comparison-subject image display-control unit 55c settles the preparation of image reading (Step S118).

When the observation-image display-control unit 55d then receives via the operation receiving unit 54 a display request to display the image observation area in which medical images for comparative image reading are to be displayed, the observation-image display-control unit 55d conducts display of the medical images displayed in the observation-image preparation area into the image observation area by maintaining the image layout (Step S119).

Figure 13:
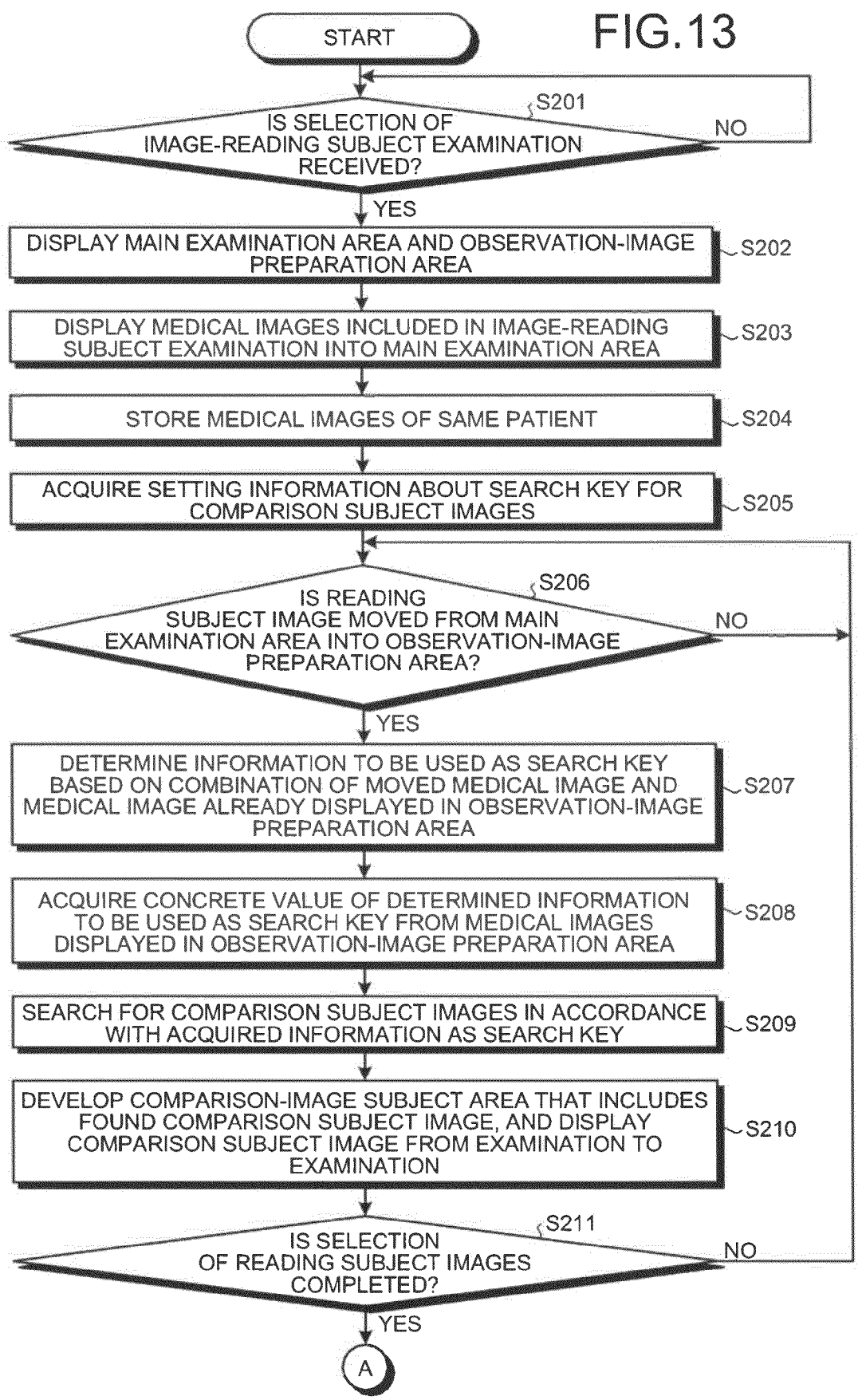
FIGS. 13 and 14 are flowcharts that depict a modification of the process procedure performed by the medical-image observation apparatus according to the first embodiment.
Figure 14:
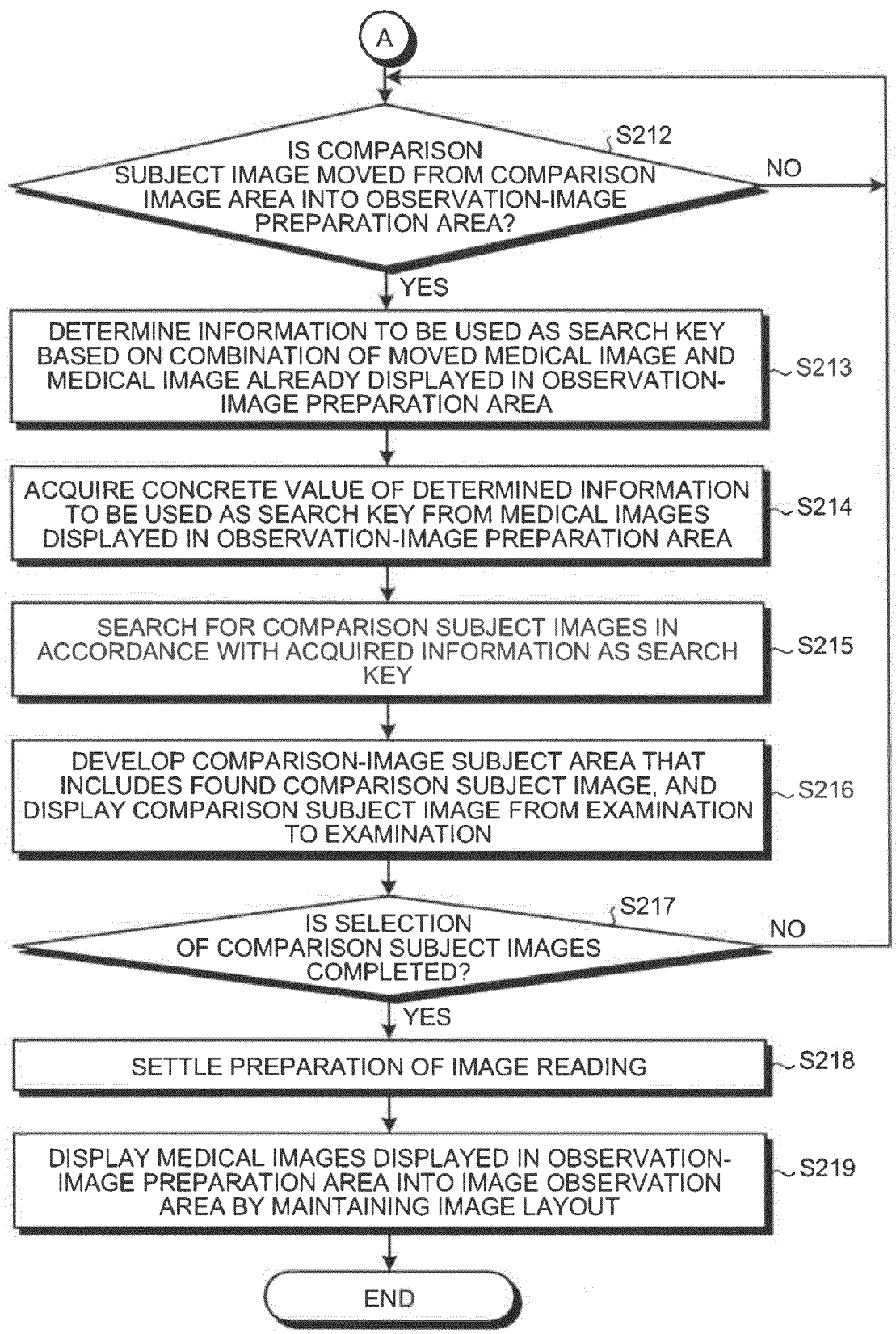

Although the process procedure of selecting a comparison subject image for each reading subject image is explained above with reference to FIGS. 11 and 12, it can be configured to select comparison subject images after reading subject images are priorly all selected. FIGS. 13 and 14 are flowcharts (1) and (2) that depict a modification of the process procedure performed by the medical-image observation apparatus 50 according to the first embodiment.

In this case, as shown in FIG. 13, to begin with, the image display-area display-control unit 55a and the reading-subject image display-control unit 55b perform processing similar to those at Steps S101 to S105 shown in FIG. 11 (Steps S201 to S205).

After that, while the operator is performing the operation of moving a reading subject image from the main examination area into the observation-image preparation area (the operation at Step S206), the comparison-subject image display-control unit 55c repeats processing similar to those at Steps S106 to S116 (Steps S206 to S210) (No at Step S211); and when the selection of all reading subject images is completed (Yes at Step S221), the comparison-subject image display-control unit 55c receives an operation of moving a comparison subject image (Step S212).

As shown in FIG. 14, while the operator is then performing the operation of moving a comparison subject image from a comparison image area into the observation-image preparation area (the operation at Step S212), the comparison-subject image display-control unit 55c repeats processing similar to those at Steps S111 to S115 shown in FIG. 12 (Steps S212 to S216) (No at Step S217); and when the selection of the comparison subject images is completed (Yes at Step S217), the comparison-subject image display-control unit 55c settles the preparation of image reading (Step S218).

When the observation-image display-control unit 55d then receives via the operation receiving unit 54 a display request to display the image observation area in which medical images for comparative image reading are to be displayed, similarly to Step S119 shown in FIG. 12, the observation-image display-control unit 55d conducts display of the medical images displayed in the observation-image preparation area into the image observation area by maintaining the image layout (Step S219).

As described above, according to the medical-image observation apparatus 50 of the first embodiment, the image display-area display-control unit 55a causes the display unit 52 to display the main examination area for displaying a thumbnail of a medical image to be read, and the observation-image preparation area for displaying a thumbnail of a medical image selected as a medical image to be used for comparative image reading. After the reading-subject image display-control unit 55b then causes the display unit 52 to display in the main examination area the thumbnail of the medical image to be read, upon receiving an operation of moving the medical image of which thumbnail is displayed in the main examination area into the observation-image preparation area, the comparison-subject image display-control unit 55c specifies a medical image to be a comparison subject based on attribution information about the moved medical image, and causes the display unit 52 to display a thumbnail of the specified medical image. Accordingly, a medical image to be a comparison subject when performing comparative image reading of medical images can be easily selected without carrying out a procedure of finding a comparison subject image by developing a thumbnail display area.

Moreover, according to the first embodiment, while at least one medical image is being displayed in the observation-image preparation area, upon receiving an operation of moving another medical image into the observation-image preparation area, the comparison-subject image display-control unit 55c specifies a comparison subject image based on a combination of attribution information about the moved medical image and attribution information about the priorly displayed medical image, so that optimal comparison subject images are displayed in accordance with various combinations of medical images to be used for comparative image reading. Accordingly, a medical image to be a comparison subject can be more easily selected.

Furthermore, according to the first embodiment, the observation-image display-control unit 55d conducts enlarged display of a medical image of which thumbnail is displayed in the observation-image preparation area in response to a request from the operator, so that a medical image that is selected as a medical image to be used for comparative image reading can be easily enlarged to an easily-viewable size. Accordingly, comparative image reading can be efficiently performed.

Moreover, according to the first embodiment, the observation-image display-control unit 55d conducts enlarged display of medical images by maintaining a layout in which the medical images are displayed in the observation-image preparation area, so that a layout when performing comparative image reading can be preliminarily determined by moving the medical images into the observation-image preparation area while considering display positions. Accordingly, comparative image reading can be more efficiently performed.

Furthermore, according to the first embodiment, when receiving an operation of moving a medical image into the observation-image preparation area, the report-information display-control unit 55e acquires report information associated with the moved medical image as a key image, and causes the display unit 52 to display the acquired report information. Accordingly, comparative image reading can be more efficiently performed by referring to relevant report information.

Explained above in the first embodiment is a case where a medical image to be used for comparative image reading is selected by moving a medical image from the main examination area or the comparison image area into the observation-image preparation area. However, the present invention is not limited to this, and can be configured such that, for example, an image layout when performing comparative image reading can be determined on the observation-image preparation area. A case configured in this way is explained below as a second embodiment of the present invention.

Figure 15:
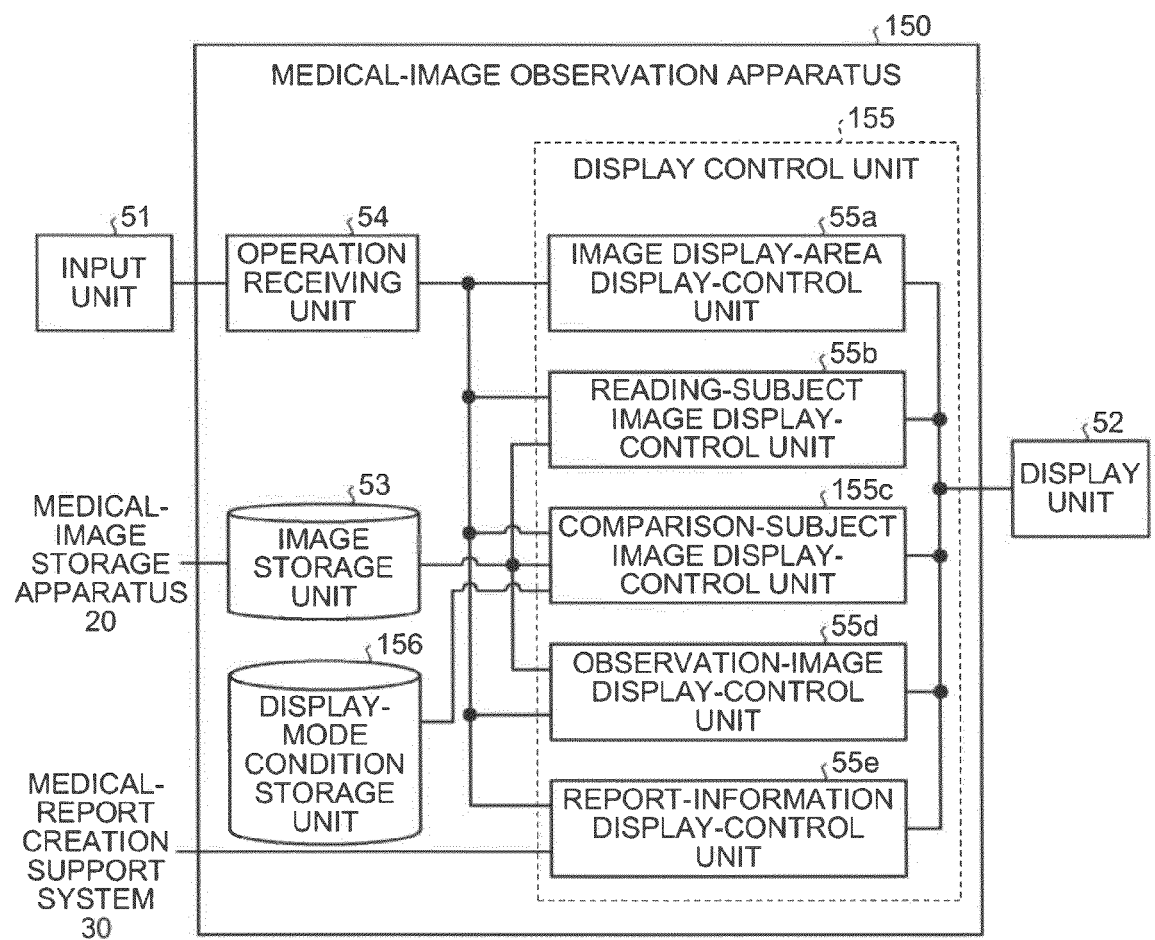
FIG. 15 is a functional block diagram that depicts a configuration of a medical-image observation apparatus according to a second embodiment of the present invention.

FIG. 15 is a functional block diagram that depicts a configuration of a medical-image observation apparatus 150 according to the second embodiment. For convenience of explanations, functional units that work similarly to those shown in FIG. 2 are assigned with the same reference numerals, and detailed explanations of them are omitted. As shown in FIG. 15, the medical-image observation apparatus 150 includes the input unit 51, the display unit 52, the image storage unit 53, the operation receiving unit 54, a display control unit 155, and a display-mode condition storage unit 156.

The display control unit 155 controls display of medical information onto the display unit 52. The display control unit 155 includes the image display-area display-control unit 55a, the reading-subject image display-control unit 55b, a comparison-subject image display-control unit 155c, the observation-image display-control unit 55d, and the report-information display-control unit 55e.

Precisely, compared with the configuration of the medical-image observation apparatus 50 shown in FIG. 2, the display control unit 155, the display-mode condition storage unit 156, and the comparison-subject image display-control unit 155c are different.

The display-mode condition storage unit 156 stores therein an image layout of medical images of which thumbnails are displayed in the observation-image preparation area as a display mode condition. The display mode condition herein is information that defines an image layout of medical images, and also called "hanging protocol".

Specifically, the display-mode condition storage unit 156 stores therein information that defines an image layout of a plurality of medical images and attribution information about the medical images to be displayed in the image layout by associating them with attribution information about the medical images. FIGS. 16A and 16B are schematic diagrams for explaining information to be stored by the display-mode condition storage unit 156 according to the second embodiment.

For example, as shown in FIG. 16A, the display-mode condition storage unit 156 stores therein an image layout for arranging four medical images in total including two rows and two columns by associating the layout with "X-ray CT (X-ray CT apparatus), which is attribution information indicating the modality. According to the example shown in FIG. 16A, as attribution information about a medical image to be arranged on the upper left, "current CT image (image taken by an X-ray CT apparatus)" and "series 1" are set. As attribution information about a medical image to be arranged on the upper right, "past CT image" and "series 1" are set.

Alternatively, as shown in FIG. 16B, the display-mode condition storage unit 156 stores therein an image layout for arranging six medical images in total including two rows and three columns by associating the layout with "X-ray CT (X-ray CT apparatus), which is attribution information indicating the modality, and "abdomen", which is attribution information indicating a scan portion. According to the example shown in FIG. 16B, as attribution information about a medical image to be arranged on the upper left, "current CT image (image taken by an X-ray CT apparatus)" and "series 1" are set. As attribution information about a medical image to be arranged on the upper center, "previous CT image, "abdomen", and "series 1" are set. As attribution information about a medical image to be arranged on the upper right, "second previous CT image, "abdomen", and "series 1" are set.

Attribution information to be set together with an image layout is not limited to "examination time", "modality", "scan portion", and "series" as shown in FIGS. 16A and 16B as examples. For example, "presence or absence of a contrast agent" or "scanning condition" can be used.

The comparison-subject image display-control unit 155c conducts display of a comparison subject image in response to an operation by the operator. FIGS. 17 to 20 are schematic diagrams for explaining display of comparison subject images controlled by the comparison-subject image display-control unit 155c according to the second embodiment.

Specifically, according to the second embodiment, upon receiving via the operation receiving unit 54 an operation of moving a reading subject image of which thumbnail is displayed in the main examination area into the observation-image preparation area, the comparison-subject image display-control unit 155c acquires a display mode condition associated with attribution information about the reading subject image by referring to information stored in the display-mode condition storage unit 156.

Subsequently, the comparison-subject image display-control unit 155c extracts thumbnails of medical images from among comparison subject images stored in the internal memory by the reading-subject image display-control unit 55b, based on attribution information about an image layout defined in accordance with the acquired display mode condition. The comparison-subject image display-control unit 155c then causes the display unit 52 to display in the comparison image area the thumbnails of the extracted medical images under a state reflecting the acquired display mode condition.

For example, it is assumed that attribution information about a reading subject image moved into the observation-image preparation area is associated with an image layout in which four images in total including two rows and two columns are arranged, and a layout in which six images in total including two rows and three columns are arranged, as display mode conditions.

Figure 17:
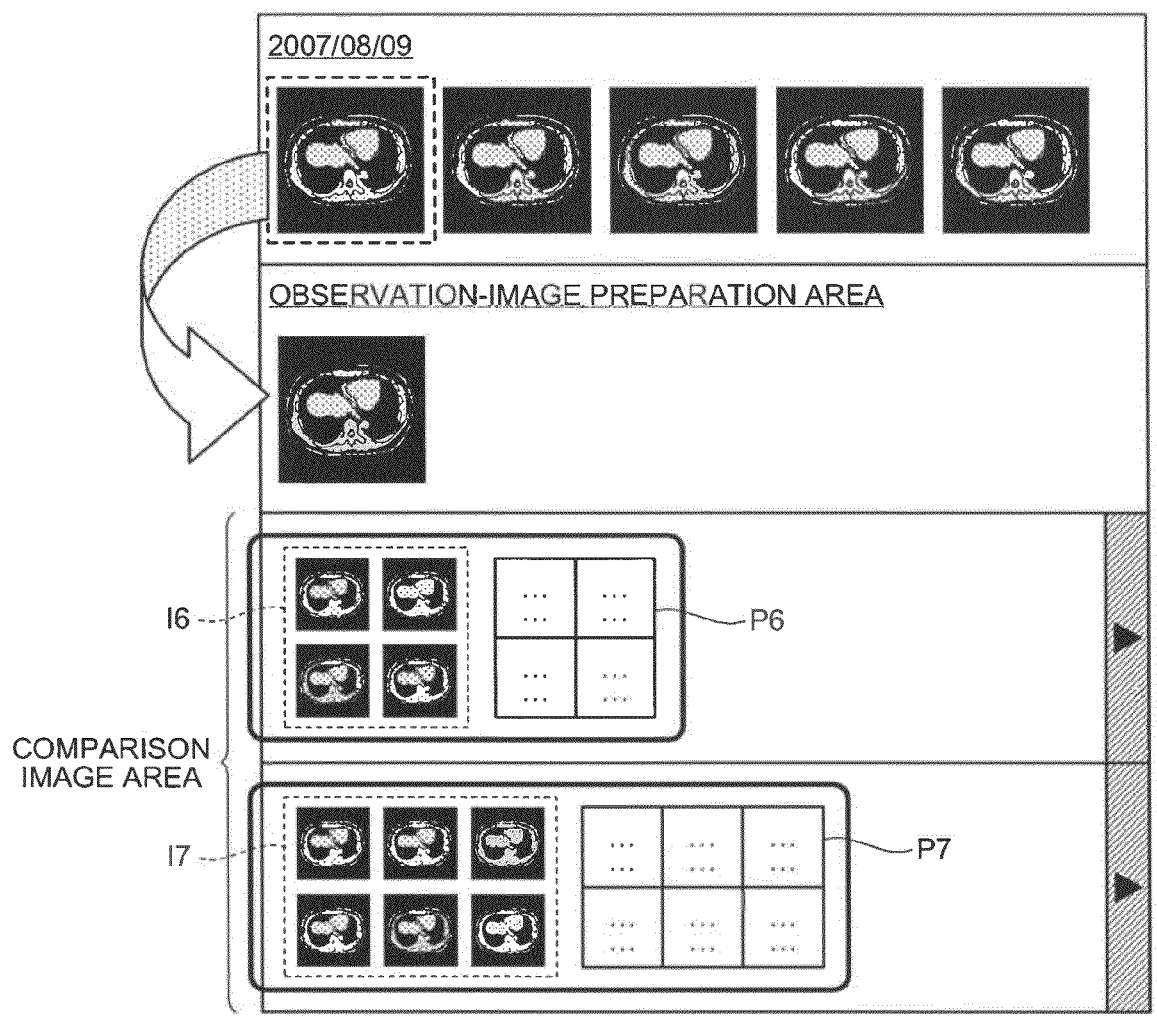

In such case, as shown in FIG. 17, the comparison-subject image display-control unit 155c causes the display unit 52 to display in respective comparison image areas thumbnail images arranged into two rows and two columns (I6 shown in FIG. 17), and thumbnail images arranged into two rows and three columns (I7 shown in FIG. 17), based on the display mode conditions associated with the attribution information about the moved reading subject image.

When displaying the thumbnail images in the comparison image areas, the comparison-subject image display-control unit 155c conducts display of information indicating attribution information about the thumbnail images in layouts similar to the thumbnails images (P6 and P7 shown in FIG. 17). Accordingly, the operator can easily grasp of what kind of attribution medical images are displayed in thumbnail.

Figure 18:
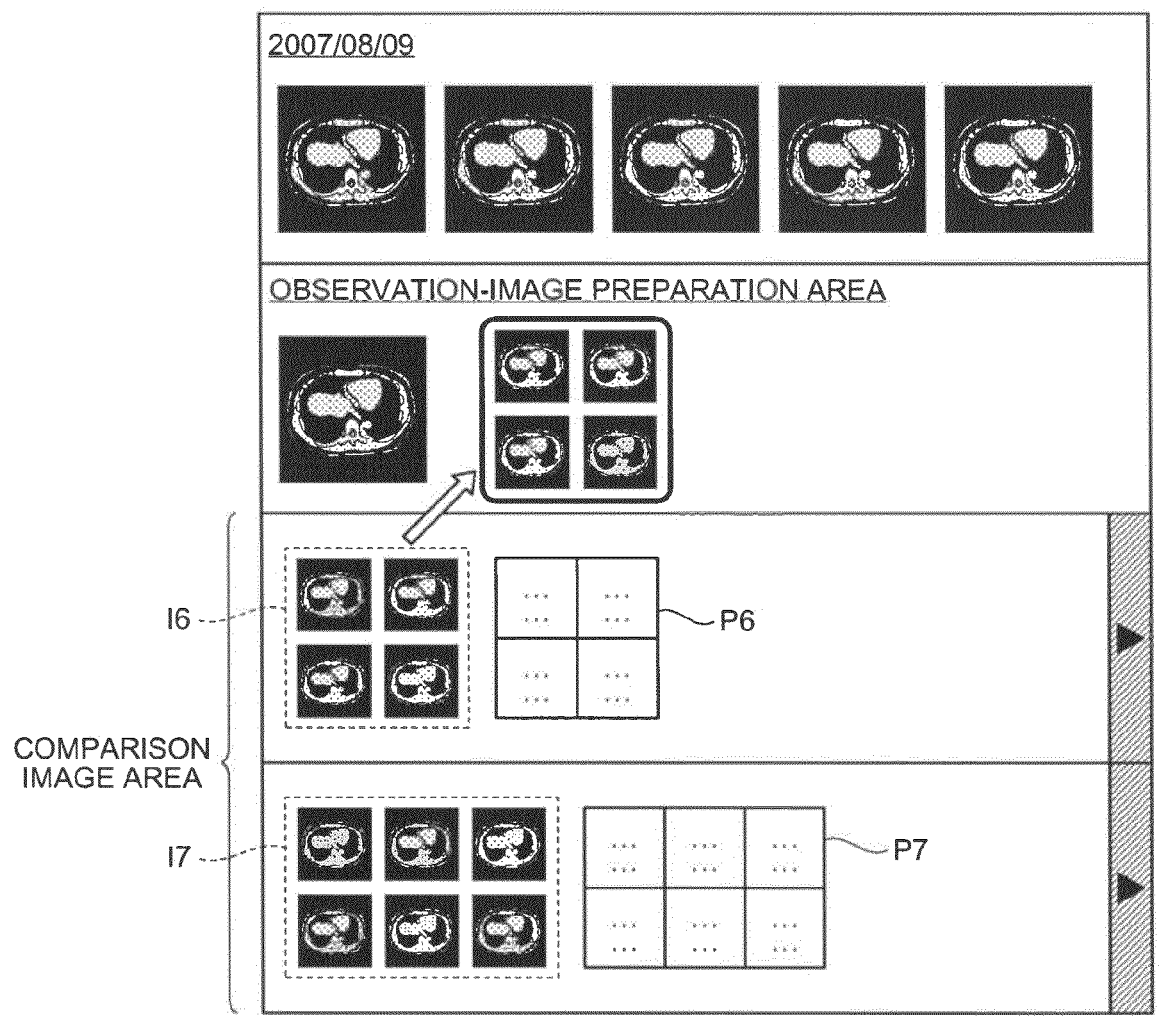

Subsequently, as shown in FIG. 18, when receiving an operation of moving a plurality of thumbnail images displayed in the certain layout in one of the comparison image areas, the comparison-subject image display-control unit 155c causes the display unit 52 to display in the observation-image preparation area the moved thumbnail images in the same image layout (I6 shown in FIG. 18).

Figure 19:
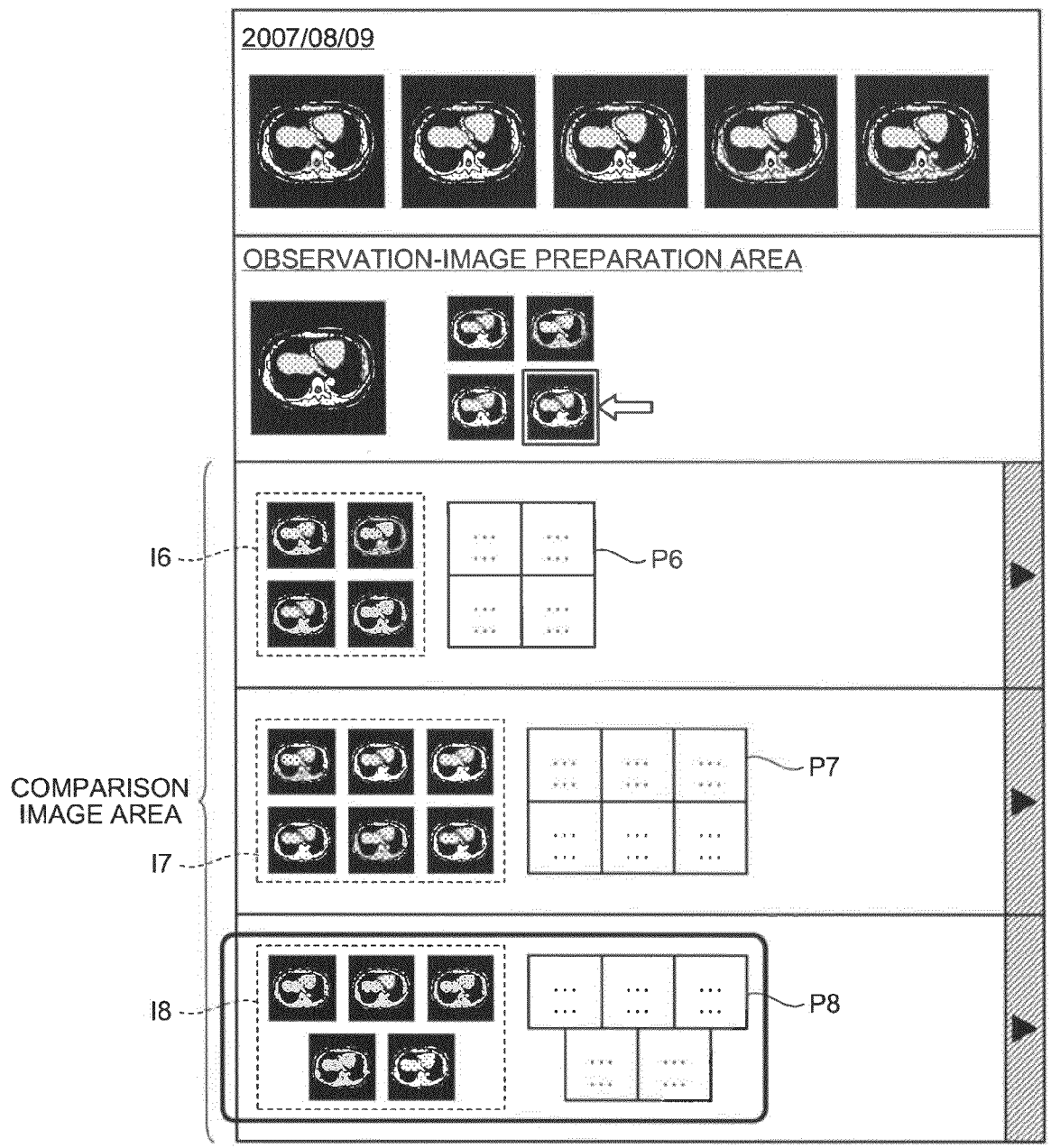

After that, as shown in FIG. 19, when the operator selects one or a plurality of medical images from among the thumbnail images displayed in the observation-image preparation area, the comparison-subject image display-control unit 155c acquires a display mode condition associated with the selected medical image. The comparison-subject image display-control unit 155c then causes the display unit 52 to display in a comparison image area medical images and attribution information in thumbnail (I8 and P8 shown in FIG. 19).

Subsequently, as shown in FIG. 20, when receiving an operation of moving a medical image displayed in the observation-image preparation area or one of the comparison image areas onto the medical images displayed in thumbnail in the certain layout in the observation-image preparation area, the comparison-subject image display-control unit 155c replaces an already displayed medical image with the moved medical image. Accordingly, the operator can create and change a display mode condition on the observation-image preparation area.

When the operator then makes an instruction to store a display mode condition, the comparison-subject image display-control unit 155c causes the display-mode condition storage unit 156 to store therein a display mode condition that is created or changed on the observation-image preparation area. Specifically, the comparison-subject image display-control unit 155c causes the display-mode condition storage unit 156 to store therein a created or changed image layout and attribution information about medical images arranged on the image layout by associating them with attribution information about a reading subject image moved from the main examination area. The display mode stored at the stage is to be similarly referred when a selection of comparison subject images is performed on and after the next time in accordance with the flow explained above.

As described above, according to the second embodiment, based on a display mode condition associated with attribution information about a medical image on which an operation of displaying into the observation-image preparation area is performed, the comparison-subject image display-control unit 155c causes the display unit 52 to display thumbnails of medical images by reflecting the display mode condition. Accordingly, an image layout when performing comparative image reading can be easily settled with a little amount of operation (for example, an amount of movement of a mouse), so that an operator's (for example, an image-reading doctor's) fatigue can be reduced.

Moreover, according to the second embodiment, the display-mode condition storage unit 156 stores therein an image layout of medical images of which thumbnails are displayed in the observation-image preparation area as a display mode condition, and the comparison-subject image display-control unit 155c conducts display of thumbnails of medical images based on the display mode condition stored by the display-mode condition storage unit 156. Accordingly, a display mode condition settled by the operator can be stored, so that an image layout can be efficiently determined on and after the next image reading by using the stored display mode condition.

Furthermore, according to the second embodiment, as attribution information for specifying a medical image to be a comparison subject, the comparison-subject image display-control unit 155c uses attribution information about a medical image selected by the operator from among medical images displayed in the observation-image preparation area. Accordingly, a comparison image area can be caused to display only medical images and an image layout that are considered by the operator to be particularly focused on, so that medical images and an image layout to be used for comparative image reading can be efficiently determined.

Although explained in the above embodiments is in a case where an operator performs an operation of moving a medical image into the observation-image preparation area, operations of displaying a medical image in the observation-image preparation area are not limited to this. For example, it can be configured such that an operation of selecting one medical image from among medical images of which thumbnails are displayed in the main examination area is received from the operator by using a mouse or a keyboard, and when such operation is received, the observation-image preparation area is caused to display the same medical image as the selected medical image, while the main examination area is cause to display the selected medical image in a not-selectable state.

According to the above embodiments, although explained above is a case where the present invention is applied to the medical-image observation apparatus 50, the present invention is not limited to this, and can be similarly applied to other apparatuses, such as the medical-image storage apparatus 20 or the medical-report creation support system 30. Moreover, the present invention can be similarly applied to the general-purpose personal computer 40 that includes a Web browser by implementing similar functions with a Web application software.

The components of each apparatus shown in the drawings in the above embodiments are conceptual for describing functions, and not necessarily to be physically configured as shown in the drawings. In other words, concrete forms of distribution and integration of the units are not limited to those shown in the drawings, and all or part of the units can be configured to be functionally or physically distributed and integrated in an arbitrary unit depending on various loads and conditions of the use.

As described above, the medical-information display apparatus and the medical-information display method according to the embodiments of the present invention are useful for performing comparative image reading of medical images, and suitable particularly when it is required to select a medical image to be a comparison subject simply and easily.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A medical information-display apparatus comprising:
a display unit that displays a first display area and a second display area; and
a display control unit that controls a display of medical information onto the display unit, wherein
the display control unit causes the display unit to display in the first display area a thumbnail of a medical image to be read, and
when receiving an operation for selecting a thumbnail in the first display area and displaying the selected thumbnail in the second display area as a thumbnail of a medical image to be used for image reading, the display control unit specifies, based on attribution information about a first medical image corresponding to the thumbnail displayed in the second display area, a second medical image to be a comparison subject with the first medical image from among medical images taken through one examination and other examinations of a patient of the first medical image, and causes the display unit to display a thumbnail of the second medical image.

2. The apparatus according to claim 1, wherein while at least one thumbnail is being displayed in the second area, when receiving an operation for displaying another medical image in the second area, the display control unit specifies a comparison subject image based on a combination of attribution information about the another medical image and attribution information about the previously displayed medical image.

3. The apparatus according to claim 1, wherein in response to a request from an operator, the display control unit conducts an enlarged display of a medical image of which thumbnail is displayed in the second display area.

4. The apparatus according to claim 3, wherein the display control unit conducts an enlarged display of the medical image by maintaining an image layout in which the medical image is displayed in the second display area.

5. The apparatus according to claim 1, wherein upon receiving an operation of displaying a medical image in the second display area, the display control unit acquires information about a report associated with the medical image as a key image, and causes the display unit to display the acquired information.

6. The apparatus according to claim 1, wherein the display unit further displays a third display area for displaying a candidate for a medical image to be used for image reading, and
the display control unit causes the third display area to display a thumbnail of the second medical image.

7. The apparatus according to claim 1, wherein the display control unit causes the display unit, based on a display mode condition associated with the attribution information about the first medical image, to display the thumbnail of the second medical image in a state of reflecting the display mode condition.

8. The apparatus according to claim 7, further comprising a display-mode condition storage unit that stores as the display mode condition an image layout of a medical image of which thumbnail is displayed in the second display area by the display control unit, wherein
    the display control unit causes the display unit to display the thumbnail of the second medical image based on a display mode condition stored by the display-mode condition storage unit.

9. The apparatus according to claim 1, wherein the display control unit uses attribution information about a medical image selected by an operator from among medical images displayed in the second display area, as the attribution information for specifying the second medical image.

10. A medical information-display method comprising:
    displaying on a display unit a first display area and a second display area;
    displaying a thumbnail of a medical image to be read on the first display area; and
    specifying, based on attribution information about a first medical image corresponding to the thumbnail displayed in the second display area, a second medical image to be a comparison subject with the first medical image from among medical images taken through one examination and other examinations of a patient of the first medical image, and causing the display unit to display a thumbnail of the second medical image, when receiving an operation for selecting a thumbnail in the first display area and displaying the selected thumbnail in the second display area as a thumbnail of a medical image to be used for image reading.

* * * * *